United States Patent [19]

Hayward et al.

[11] Patent Number: 5,585,109

[45] Date of Patent: Dec. 17, 1996

[54] COSMETIC DELIVERY SYSTEM FOR SALICYLIC ACID AND PROCESS FOR PREPARATION OF SAME

[76] Inventors: James A. Hayward, 4 Chuck Ct., Port Jefferson, N.Y. 11777; Mindy S. Goldstein, 31 Southwick Ct., Plainview, N.Y. 11803; Miriam Brown, 275 Candee Ave., Sayville, N.Y. 11782; Joseph D. Ceccoli, 26 Neil Dr., Farmingville, N.Y. 11768

[21] Appl. No.: 518,956

[22] Filed: Aug. 24, 1995

Related U.S. Application Data

[63] Continuation of Ser. No. 36,529, Mar. 24, 1993, abandoned.

[51] Int. Cl.$^6$ .................................................. A61K 9/127
[52] U.S. Cl. ............................................................ 424/450
[58] Field of Search ................................. 424/450, 401, 424/417, 420; 428/402.2; 514/177, 178, 179

[56] References Cited

U.S. PATENT DOCUMENTS

| | | | |
|---|---|---|---|
| 4,708,861 | 11/1987 | Popescu et al. | 424/1.1 |
| 4,755,387 | 7/1988 | Tzeghai et al. | 424/450 |
| 4,816,247 | 5/1989 | Desai et al. | 424/80 |
| 4,895,727 | 1/1990 | Allen | 424/642 |
| 4,944,949 | 7/1990 | Story et al. | 424/451 |
| 4,999,348 | 3/1991 | Cioca et al. | 514/171 |
| 5,000,941 | 5/1991 | Chernack | 424/49 |
| 5,049,392 | 9/1991 | Weiner et al. | 424/450 |
| 5,075,113 | 12/1991 | DuBois | 424/450 |
| 5,085,856 | 2/1992 | Dunphy et al. | 424/64 |
| 5,114,928 | 5/1992 | Gajdos et al. | 514/25 |
| 5,133,965 | 7/1992 | Fountain | 424/446 |
| 5,145,675 | 9/1992 | Won | 424/78.31 |
| 5,151,534 | 9/1992 | Schroot et al. | 554/88 |
| 5,154,930 | 10/1992 | Popescu et al. | 424/489 |

FOREIGN PATENT DOCUMENTS

| | | |
|---|---|---|
| 202621 | 5/1986 | European Pat. Off. . |
| 211647 | 2/1987 | European Pat. Off. . |
| 249561 | 6/1987 | European Pat. Off. . |
| 2040954 | 1/1971 | France . |
| 2344290 | 3/1977 | France . |

OTHER PUBLICATIONS

*Pharmazie*, vol. 42, No. 7, 1987, pp. 102–103.
Hayward, J. A., and Smith, W. P., "Potential Applications of Lipsomes in Cosmetic Science," *Cosmetic and Toiletries*, 105, 47–54 1990.
Wilkinson, J. B. and Moore, R. J., *Harry's Cosmeticology*, 7th Ed., 1982, Chemical Pub. Co., Inc., New York, NY pp. 19, 45, 122, 687, and 366.

*Primary Examiner*—Gollamudi S. Kishore
*Attorney, Agent, or Firm*—John F. Vodopia

[57] ABSTRACT

A cosmetic composition and salicylic acid delivery system includes membrane lipid bylayers formed as liposomes and un-neutralized salicylic acid localized within the lipidic bylayers of the liposomes. Other cosmetic ingredients may be located either within the membrane compartment or in either the external or internal aqueous compartments relative the liposomal bylayers. The composition also includes an organic, water-soluble membrane-impermeant base and water.

11 Claims, 1 Drawing Sheet

% SALICYLIC ACID RECOVERED
IN VIVO PENETRATION STUDY

COSMETIC DELIVERY SYSTEM FOR SALICYLIC ACID AND PROCESS FOR PREPARATION OF SAME

This application is a continuation of U.S. patent application Ser. No. 08/036,529, filed Mar. 24, 1993, now abandoned.

BACKGROUND OF THE INVENTION

1. Field of the Invention

The present invention relates to liposomal dispersions containing un-neutralized salicylic acid and a process for their preparation. More particularly, the present invention relates to a cosmetic dispersion that allows for the incorporation of large amounts of salicylic acid within the hydrophobic compartment of the liposomal bilayer, without the necessity of pre-neutralization or salt formation of the corresponding salicylate, while simultaneously permitting the pH of the external aqueous compartment to be adjusted with soluble organic bases.

2. The Prior Art

Salicylic acid is an active ingredient long-known to those skilled in the formulation of cosmetic and topical products. Dandruff has been treated with ointments containing 2 percent salicylic acid. As a keratolytic agent, salicylic acid will soften and swell the epidermis. At concentrations higher than 2 percent, salicylic acid is an efficacious anti-acne agent and is bactericidal. The formation of salts of salicylic acid, such as sodium salicylate formed by the combination of salicylic acid and sodium hydroxide, greatly improves the water solubility of the free acid, but substantially modifies the biological response to salicylic acid.

Salicylic acid is nearly insoluble in water (limit of solubility approximately 0.2 percent at room temperature). When incorporated into cosmetic solutions, salicylic acid requires the addition of cosolvents such as ethanol, isopropanol or dimethylsulfoxide. These solutions exhibit low pH (approximately 2), and as a consequence may be irritating to the skin. Development of aesthetic cosmetic formulations under these constraints of pH greatly limits the range of formulation types. For example, hydrocolloid gels will not form at this extreme of pH. Many other cosmetic ingredients are rendered unstable under these conditions.

A general reference for the formulation of cosmetic compositions containing salicylic acid follows:

Wilkinson, J. B. and Moore, R. J. *Harry's Cosmeticology (Seventh Edition)*, 1982, Chemical Publishing Co., Inc., New York, N.Y., pp. 19, 45, 122, 687, 366.

A general refernce for the application of liposomes to cosmetics follows:

Hayward, J. A. and Smith, W. P. *Potential Applications of Liposomes in Cosmetic Science*, in Cosmetic and Toiletries, 105: 47–54, 1990.

The Won U.S. Pat. No. 5,145,675 is related to a topical delivery system for active ingredients such as salicylic acid, whereby controlled release is achieved by the gradual desorption of the active ingredient from solid, porous particles.

The Cioca et al U.S. Pat. No. 4,999,348 is related to cosmetic and pharmaceutical compositions containing liquid crystals and liposomes, and methods of incorporating such ingredients into cosmetic formulations.

The Desai et al U.S. Pat. No 4,816,247 is related to emulsions of ionizable hydrophobic drugs including hydroxybenzoic acid (salicylic acid).

The Popescu et al. U.S. Pat. 4,708,861 is related to liposome gel compositions.

The Allen U.S. Pat. No. 4,895,727 relates to topical treatment methods which utilize water-soluble zinc compound to enhance the reservoir effect of active ingredients in the skin, including salicylic acid.

The Story and Flynn U.S. Pat. No. 4,944,949 relates to micellar dispersions of non-steroidal anti-inflammatory drugs (NSAID's), such as salicylic acid, with surfactants such as polyethoxylated nonionics.

The Shroot et al. U.S. Pat. No. 5,151,534 relates to eicosenoid lipids and their application in pharmacy and cosmetics. These lipids may be formulated with salicylic acid and may be incorporated into liposomes.

The Tzeghai and Leis U.S. Pat. No. 4,755,387 relates to oral therapeutics, such as salicylic acid, which have a coating of lipids to provide release of the therapeutic in the intestines. The lipid coatings are non-liposomal, and are comprised of neutral lipids and esters.

The DuBois U.S. Pat. No. 5,075,113 relates to phospholipid-based emulsions of paraffins which may contain salicylic acid.

The Gajdos and Metzen U.S. Pat. No. 5,114,928 relates to solid dosage forms comprised of non-liposomal phospholipid and utilizes salicylic acid as a stabilizer.

The Dunphy et al. U.S. Pat. No. 5,085,856 relates to a formulation for a water-in-oil emulsion comprising phospholipids which may include liposomes, and, within the emulsion, salicylic acid.

The Weiner and Fielder U.S. Pat. No. 5,049,392 relates to a method of producing liposomes specifically via osmotic shock; the resultant liposomes may contain NSAID's including salicylic acid.

The Fountain U.S. Pat. No. 5,133,965 relates to a wound dressing comprised of liposomes generated by a solvent-dilution method; the resultant liposomes may contain salicylic acid.

SUMMARY OF THE INVENTION

It is therefore an object of the present invention to provide a liposomal composition, particularly a topical formulation, and a process for its preparation, that permits the generation of liposomes containing salicylic acid, that allows the adjustment of the pH of the external aqueous compartment to pH ranges approaching neutrality, and that ensures that the greater proportion of the salicylic acid in the formulation remains as the free acid.

Other objects and features of the present invention will become apparent when considered in combination with the following summary and detailed description of certain preferred embodiments and examples of the present invention.

The foregoing and related objects are achieved by providing a cosmetic composition containing:

a) an effective amount of polar lipids known to form, either alone or in combination, liposomal bilayers;

b) an effective amount of salicylic acid;

c) an effective amount of a polar, membrane-impermeant, water-soluble organic base; and, d) the balance up to 100 percent by weight of water based upon the total composition weight.

In addition, the composition may also contain an effective amount of any other suitable cosmetic or pharmaceutic ingredient, amoung which and specifically suited to the purpose are any of the many commercially available raw materials intended to function as antioxidants, preservatives, anti-inflammatory agents, and hydrocolloids.

The cosmetic liposomes of the invention can optionally also comprise other ingredients as are conventionally employed in cosmetic products. Examples of other ingredients include but are not limited to perfumes, colorants such as staining dyes and pigments, humectants, anti-dandruff agents, anti-acne agents, germicides, sunscreens, emollients, vitamins, sterols and other lipids.

Particularly preferred pigments, when present, include calcium oxide, barium oxide and aluminum oxide, iron oxides, titanium dioxide, and mica.

Particularly preferred humectants include butylene glycol, glycerol, sorbitol and other polyols.

Particularly preferred antidandruff agents include selenium, selenium salts, resourcinol and coal tar.

Particularly preferred anti-acne agents include benzoyl peroxide and resourcinol.

Particularly preferred germicides include the parabens, kathon CG, phenoxyethanol and germall 115.

Particularly preferred sunscreens include octyl methoxycinnimate and butyl methoxydibenzoylmethane.

Particularly preferred emollients include cyclomethicone, dimethicone, and lanolin derivatives.

Particularly preferred hydrocolloids include hyaluronic acid, guar, carrageenan, alginic acid, polymethacrylates and their derivatives.

Particularly preferred vitamins include vitamin E, vitamin A palmitate and Vitamin C.

Particularly preferred sterols include sitosterol, stigmasterol, phytosterols and cholesterol.

Particularly preferred other lipids include ceramides, cerebroside and other sphingolipids The preferred method of manufacture involves extrusion under conditions of extremely high pressure generated by commercially available equipment such as the Microfluidizer (Microfluidics Corp., Newton, Mass.). The liposomes are produced in the presence of insoluble salicylic acid and the bilayer-forming lipids devoid of any organic bases or buffers. After production, the pH of the external aqueous compartment is adjusted with a membrane-impermeant organic base.

Particularly preferred membrane lipids include the synthetic phospholipids such as dipalmitoylphosphatidylcholine, natural phospholipids such as soya lecithin or egg yolk lecithin, phosphatidylethanolamines, phosphatidylserines, cereamides, cerebrosides, and phosphatidylglycerides.

Particularly preferred organic bases include the basic amino acids such as arginine, lysine and glutamine, and triethanolamine.

An effective amount of the membrane-forming lipid phase is preferably from 0.1% to 10% by weight, more preferably from 0.5% to 5.0% by weight, and most preferably from 1.0% to 4.0% by weight, based upon the total composition weight.

An effective amount of salicylic acid is from 0.05% to 20% by weight, more preferably from 1% to 15% by weight, and most preferably 5% to 12% by weight, based upon the total composition weight.

An effective amount of organic base is from 0.05% to 25% by weight, more preferably from 1% to 20% by weight, and most preferably from 2 to 15% by weight, based upon the total composition weight.

The cosmetic composition of the invention is useful as a moisturizer, a moisturizing gel, an anti-dandruff lotion, a cleanser and a toner.

BRIEF DESCRIPTION OF THE DRAWING

The present invention will now be described in greater detail with reference being made to the drawing and the following examples and preferred embodiments. It should, of course, be recognized that the drawing and the following examples and preferred embodiments of the invention are intended solely for the purpose of illustration, and are not intended as limiting the scope thereof.

DETAILED DESCRIPTION OF THE PREFERRED EMBODIMENTS

Figure 1:
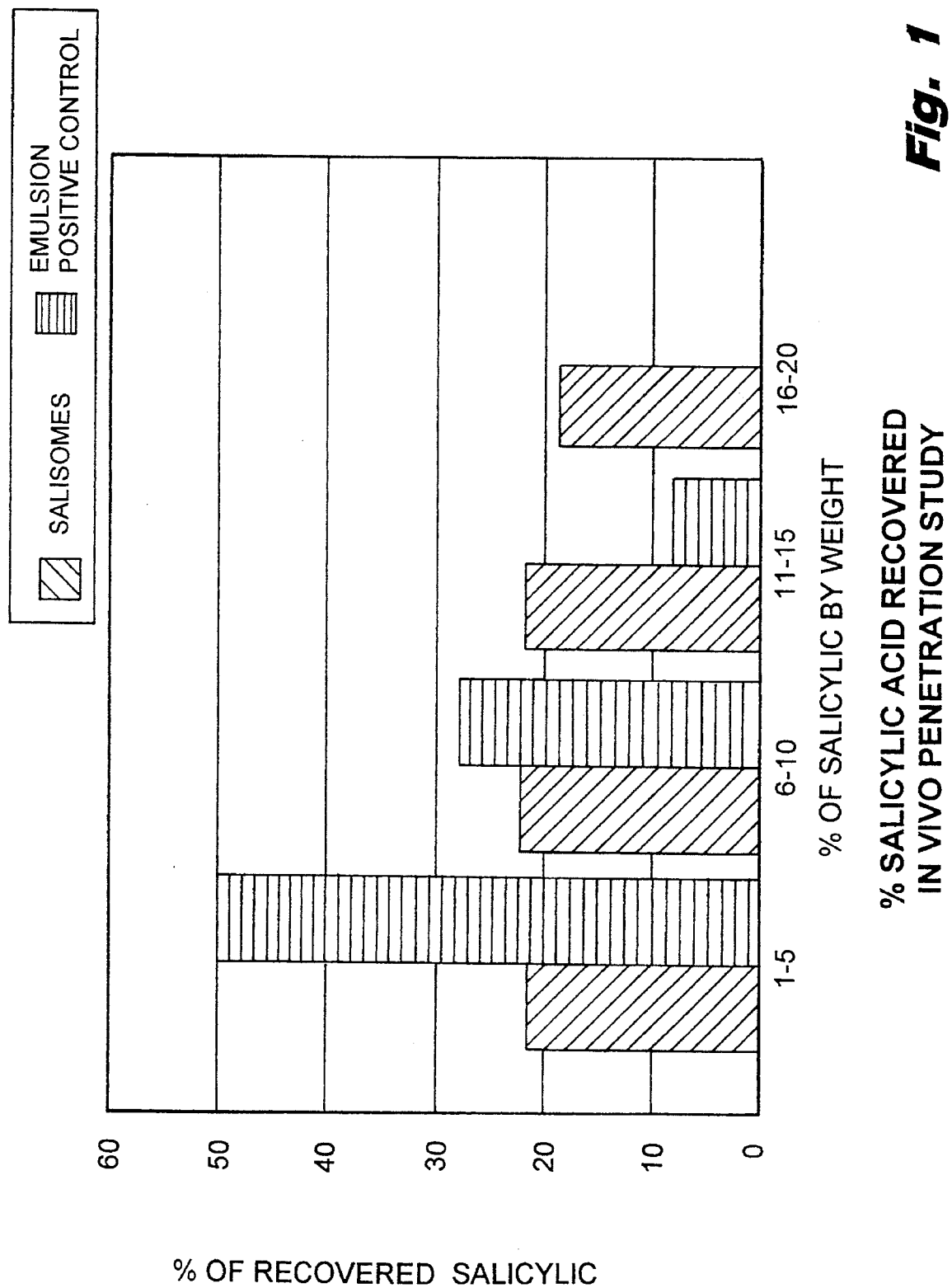
FIG. 1 represents a penetration study for salicylic acid recovered from skin strips of human panalists following application of liposomes containing salicylic acid.

In a preferred embodiment, the cosmetic composition of the present invention comprises:

a) about 0.1% to 10% by weight of a membrane-forming lipid phase;

b) about 0.05% to 20% by weight of salicylic acid;

c) about 0.05% to 25% by weight of arginine or a similar water-soluble organic base;

d) about 40% to 99.8% by weight of water;

e) 0% to about 20% by weight of other suitable cosmetic ingredients, and with all weight percentages based upon the total % composition weight.

The advantages of the present invention include the fact that the cosmetic composition has the unexpected ability to sustain a neutral pH (7.0) in the external aqueous milieu, without neutralizing the salicylic acid to the corresponding salicylate. Once neutralized, the bulk dispersion can be utilized in a wide array of finished product types.

In a more preferred embodiment, the cosmetic composition of the present invention comprises:

a) about 0.5% to 5% by weight of a membrane-forming lipid phase;

b) about 1.0% to 15% by weight of salicylic acid;

c) about 1.0% to 20% by weight of arginine or a similar water-soluble organic base;

d) about 50% to 98.5% by weight of water;

e) about 1% to 20% by weight of other suitable cosmetic ingredients, and with all weight percentages based upon the total % composition weight. In a most preferred embodiment, the cosmetic composition of this invention comprises:

a) about 1% to 4% by weight of a membrane-forming lipid phase;

b) about 5% to 12% by weight of salicylic acid;

c) about 2% to 15% by weight of arginine or a similar water-soluble organic base;

d) about 60% to 90% by weight of water;

e) about 5% to 15% by weight of other suitable cosmetic ingredients, and with all weight percentages based upon the total % composition weight.

The ingredients used in the composition of this invention should be of a quality or purity (such as U.S.P. or N.F.) suitable for cosmetic use and should be compatible when used together in a particular composition. Unless indicated otherwise, the physical properties of the components of the composition of the present invention specified herein are the properties of these components before they are mixed with the composition's other ingredients.

Among the commercially available suitable membrane forming lipids are the various purified soya lecithins available from Natterman (Cologne, Germany), Lucas Meyer (Ill.), Avanti Polar Lipids (N.Dak.), and Nikko Chemical (Tokyo, Japan).

Among the commercially suitable soluble organic bases are L-Arginine, L-Lysine, L-Glutamine, available from Tanabi (Woodcliff lake, N.J.) and Triethanolamine, available from Acro Chemical Company (Farmingdale, N. Y.).

Salicylic acid is available from Universal Preserv-A-Chem, Inc. (Brooklyn, N.Y.).

The composition of the present invention may be prepared by the following process steps, which are carried out at room temperature (25C ) under 1 atmosphere pressure of argon gas (to limit any opportunity for oxidation):

a) Use of a marine or propellar-type mixer to disperse the membrane-forming lipid in the total quantity of water available to the formulation. In this first embodiment, the mixing occurred at 500 to 1500 rpm and lasted for 1 hour. The remaining water-insoluble phases are then added to the wetted lipids, along with the salicylic acid and any germicides or preservatives. Any additional cosmetic excipients or active ingredients are then added to the batch. In this second embodiment, the mixing was continued at 500 to 1500 rpm for 1 hour with caution to avoid vortex and entrainment of air.

b) In order to facilitate hydration of the batch prior to high-shear processing, the batch was then homogenized with a rotor/stator-type homogenizer running at 3,000 rpm for 30 minutes.

c) At this stage the batch was subjected to high-shear processing, specifically microfluidization. In this process, the liquid is extruded through two 100 micron pores. The jetting streams collide within an interaction chamber, and then the liquid is extruded to ambient pressure. The combination of shear and pressure change completes the dispersion of the insoluble phases and produces liposomes as verified by freeze-fracture electron microscopy.

d) The pH of the batch at this stage is acidic (pH approximately 2.0) due to the limited solubility of salicylic acid in water (approximately 0.2%). A batch titration was then performed with arginine to acheive a final pH of 6.5 to 7.5. The amount of arginine required is determined by the total availability of titratable groups. However, less than 1% salicylic acid is neutralized by this process.

e) Finally, any necessary additional cosmetic ingredients meant to occupy solution volumes outside the liposomes may be added. Such materials might include thickeners or other rheologic agents, emollients, humectants and germicides.

The above procedure is generic to all of the specific types of compositions, and may be modified as necessary to achieve the preparataion of a specific final product. Different ingredients may require modification in the order of addition of materials, depending on whether the intentionis to locate the ingredient internal or external to the liposome, whether the ingredient is water-soluble, or whether the ingredient behaves as an acid or base.

EXAMPLES

| Example 1 (Salicylic Acid Liposome) | | |
|---|---|---|
| Phase | Ingredient | Parts by Weight |
| 1 | Lecithin | 1.0 |
| 1 | Water | 83.0 |
| 2 | Salicylic Acid | 10.0 |
| 2 | Phenonip | 1.0 |
| 2 | Vitamin E Acetate | 1.0 |
| 3 | Arginine | 4.0 |

The ingredients in Phase 1 were mixed by a propeller rotating at 500 to 1,500 rpm for one hour. The ingredients of Phase 2 were added, and mixing continued for an additional one hour. The batch was then subjected to high-shear extrusion at 12,000 psi of pressure through a 100 micron pore. Dynamic laser light scattering revealed a particle diameter of 200 nanometers. Carboxyfluoroscein labeling indicated intact liposomes. Freeze-fracture transmission electron microscopy substantiated the presence of vesicles. After microfluidization, the arginine was added, and the pH increased from 2.0 to 6.7.

FIG. 1 contrasts the penetration of salicylic acid into the epidermis of the volar forearm of human panelists. The degree of penetration was determined by HPLC analysis of solubilized Scotch Tape strips. A control comprised of a sodium sterate emulsion containing 10 percent salicylic acid was prepared. Both the experimental liposome and the control emulsion were diluted 1 to 10 in a gel of polymethacrylate and applied at equivalent sites. The figure reveals that the penetration of salicylic acid was facilitated by liposomal inclusion. The level of liposomal salicylic acid was found to be, and continued to be, safe, non-irritating, moisturizing product.

| Example 2 (Moisturizing Liposome) | | |
|---|---|---|
| Phase | Ingredient | Parts by Weight |
| 1 | Lecithin | 2.0 |
| 1 | Sitosterol | 0.5 |
| 1 | Water | 84.5 |
| 1 | Trehalose | 1.0 |
| 1 | NaPCA | 1.0 |
| 2 | Salicylic Acid | 5.0 |
| 2 | Phenonip | 1.0 |
| 2 | Vitamin E Linoleate | 1.0 |
| 2 | Vitamin A Palmitate | 1.0 |
| 3 | Arginine | 3.0 |

The product was processed utilizing a procedure analogous to that described above for Example 1. The sample was diluted 1 to 4 in a 0.5 percent polymethacrylate gel and applied to the skin. After two hours, the final product was found to be, and continued to be, safe, non-irritating, moisturizing product.

| Example 3 (Anti-Acne Liposome) | | |
|---|---|---|
| Phase | Ingredient | Parts by Weight |
| 1 | Lecithin | 2.0 |
| 1 | Cholesterol | 0.3 |
| 1 | Glycine | 1.0 |
| 1 | Resourcinol | 0.1 |
| 1 | Water | 86.6 |
| 2 | Salicylic Acid | 5.0 |

-continued

Example 3 (Anti-Acne Liposome)

| Phase | Ingredient | Parts by Weight |
|---|---|---|
| 2 | Chlorphenesin | 2.5 |
| 3 | Argine | 2.5 |

The product was processed utilizing a procedure analogous to that described above for Example 1. The sample was diluted 1 to 4 in a 0.5 percent polymethacrylate gel. After dilution, the product was innoculated with $1\times10^7$ cfu per gram of p.acne. At 48 hours, no bacteria could be detected. The final product was applied to the skin beneath the eye of an adult human male. After two hours, no indication of irritation was present, and the product continued to be a safe and non-irritating anti-acne formulation.

Example 4 (Moisturing Liposome Gel)

| Phase | Ingredient | Parts by Weight |
|---|---|---|
| (a) Preproduct | | |
| 1 | Lecithin | 2.0 |
| 1 | NaPCA | 1.0 |
| 1 | Glycine | 1.0 |
| 1 | Trehalose | 1.0 |
| 1 | Water | 86.6 |
| 2 | Salicylic Acid | 2.0 |
| 2 | Chlorphenesin | 2.5 |
| 3 | Arginine | 0.5 |
| (b) Final Product | | |
| 4 | Butylene glycol | 3.1 |
| 4 | Carbomer 941 | 0.3 |

The product was processed utilizing a procedure analogous to that described above for Example 1. The sample was found to have a viscosity of 28,000 centipoise. The final product was topically applied to the skin of the forearm of adult human male. After two hours, no indication of irritation was present, and the product continued to be a safe and non-irritating moisturizer.

What is claimed is:

1. A cosmetic composition for the containment and delivery of free salicylic acid, comprising:
   a.) liposomes, said liposomes comprising lipidic bilayers which form a lipidic, hydrophobic environment surrounded by an aqueous core:
   b.) salicylic acid, a substantial portion of which is localized within the lipidic, hydrophobic environment of the liposomal bilayers;
   c.) a membrane-impermeant, water-soluble organic base; and
   d.) water, wherein an amount of said base may be varied within said composition thereby varying its pH without affecting said salicylic acid localized within said lipidic, hydrophobic environment.

2. A cosmetic composition comprising:
   a.) about 0.1% to about 10% by weight of a lipid phase substantially all of which is structurally arranged to form liposomal bilayer vesicles;
   b.) about 0.05% to about 20% by weight of salicylic acid;
   c.) about 0.05% to about 25% by weight of a water-soluble organic base;
   d.) about 40% to about 99.8% by weight of water;
   e.) about 0% to about 20% by weight of cosmectic ingredients;
   wherein all weight percentages are based upon total composition weight.

3. The cosmetic composition of claim 1, wherein a weight percent of said salicylic acid in said composition is approximately ten, and wherein about ninety-five percent of said ten weight percent of said salicylic acid is localized in said lipidic, hydrophobic environment of said liposomal bilayers.

4. The cosmetic composition of claim 1, wherein less than about 2 percent of said salicylic acid exists intravesicular said liposomes, and less than about 2 percent of said salicylic acid exists extravesicular said liposomes.

5. The composition of claim 1, wherein said organic base includes Arginine.

6. The cosmetic composition of claim 2, wherein said weight percent of said lipid phase is about one, said weight percent of said salicylic acid is about ten, said weight percent of said water-soluble organic base is about four, said weight percent of said water is around eighty-three, and said weight percent of said cosmetic ingredients is around two.

7. The cosmetic composition of claim 6, wherein said water soluble organic base is Arginine.

8. The cosmetic composition of claim 6, wherein said cosmetic ingredients are selected from the group consisting of phenonip and vitamin A acetate.

9. A liposome delivery system for the containment and delivery of free salicylic acid, comprising:
   salicylic acid;
   liposome vesicles formed of lipidic bilayers, such that first environment is formed in a space surrounded by said bilayers and a second environment is formed in a space external to said bilayers,
   water;
   wherein substantially all said salicylic acid present in said system is present within said liposome vesicles and wherein a pH of said first environment may be maintained in a state which is distinct from that state of said second environment.

10. The liposome delivery system of claim 9, wherein substantially all of said salicylic acid is localized within said lipidic bilayers.

11. The liposome delivery system of claim 10, wherein greater than 95 percent of said salicylic acid resides in said lipidic bilayers.

* * * * *